(12) United States Patent
Hongo et al.

(10) Patent No.: US 9,056,896 B2
(45) Date of Patent: Jun. 16, 2015

(54) METHOD FOR REMOVING VIRUSES FROM HIGH CONCENTRATION MONOCLONAL ANTIBODY SOLUTION

(75) Inventors: Tomoko Hongo, Miyazaki (JP); Masayasu Komuro, Miyazaki (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 689 days.

(21) Appl. No.: 13/260,419

(22) PCT Filed: Mar. 26, 2010

(86) PCT No.: PCT/JP2010/002219
§ 371 (c)(1),
(2), (4) Date: Dec. 12, 2011

(87) PCT Pub. No.: WO2010/109920
PCT Pub. Date: Sep. 30, 2010

(65) Prior Publication Data
US 2012/0077963 A1    Mar. 29, 2012

(30) Foreign Application Priority Data

Mar. 27, 2009  (JP) ................................. 2009-078171

(51) Int. Cl.
A23J 1/00    (2006.01)
C07K 1/34    (2006.01)
C07K 16/06   (2006.01)

(52) U.S. Cl.
CPC ................. C07K 1/34 (2013.01); C07K 16/065 (2013.01)

(58) Field of Classification Search
None
See application file for complete search history.

(56) References Cited

U.S. PATENT DOCUMENTS

| 2003/0190316 A1 | 10/2003 | Kakuta et al. |
| 2003/0232969 A1 | 12/2003 | Lengsfeld et al. |
| 2004/0197324 A1 | 10/2004 | Liu et al. |
| 2005/0158303 A1 | 7/2005 | Liu et al. |
| 2006/0142549 A1* | 6/2006 | Takeda et al. .................. 530/351 |
| 2007/0053900 A1 | 3/2007 | Liu et al. |
| 2007/0086995 A1 | 4/2007 | Liu et al. |
| 2009/0280129 A1 | 11/2009 | Liu et al. |
| 2010/0158898 A1 | 6/2010 | Liu et al. |
| 2012/0064086 A1 | 3/2012 | Liu et al. |

FOREIGN PATENT DOCUMENTS

| EP | 1 457 497 A1 | 9/2004 |
| JP | 2001-335509 A | 12/2001 |
| JP | 2003-274941 | 9/2003 |
| JP | 2007-524602 | 8/2007 |
| WO | 98/30230 | 7/1998 |
| WO | 02/13860 | 2/2002 |
| WO | WO 2004001007 A2 * | 12/2003 |
| WO | 2008/008872 | 1/2008 |
| WO | 2008/156124 | 12/2008 |

OTHER PUBLICATIONS

Extended European Search Report issued with respect to counterpart European Application No. 10755721.7, dated Jan. 2, 2013.
Yunioki et al., "Extend of hepatitis E virus elimination is affected by stabilizers present in plasma products and pore size of nanofilters", *Vox Sanguinis*, vol. 95, Jul. 9, 2008, pp. 94-100.
Hongo-Hirasaki et al., "Removal of small viruses (parvovirus) from IgG solution by virus removal filter Planova20N", Journal of Membrane Science, 2006, pp. 3-9.
"Soshiki Baiyo no Gijutsu", Asakura Shoten, 1982, pp. 186-187.
Ide, "Cellulose Chikushi Maku (Planova) ni yoru Virus Bunri", Cellulose Communications, 2007, pp. 17-19.
Search report from International Application No. PCT/JP2010/002219, mail date is Apr. 27, 2010.
International Preliminary Report on Patentability for International Application No. PCT/JP2010/002219, mail date is Oct. 6, 2011.
Manabe, "Removal of Virus Through Novel Membrane Filtraction Method", Dev. Biol. Stand. 1996, vol. 88, pp. 81-90.
H. Brandwein et al., "Membrane filtration for virus removal", Dev. Biol. 1999, vol. 102, , pp. 157-163.
Hazael Aranha-Creado et al., "Clearance of Murine Leukaemia Virus from Monoclonal Antibody Solution by a Hydrophilic PVDF Microporous Membrane Filter", Biologicals (1998) 26, , pp. 167-172.
L. Moce-Llivina et al., "Comparison of polyvinylidence fluoride and plyether sulfone membranes in filtering viral suspensions", J. of Virological Methods 109(2003) , pp. 99-101.

* cited by examiner

Primary Examiner — Daniel E Kolker
Assistant Examiner — James Rogers
(74) Attorney, Agent, or Firm — Greenblum & Bernstein, P.L.C.

(57) ABSTRACT

An object of the present invention is to provide a method for removing even small viruses from a high concentration monoclonal antibody solution using a membrane, and thus for recovering the antibody within a short time at high yield in the form of a filtrate. The present invention provides a method for producing a preparation containing a monoclonal antibody, which comprises a step of removing viruses by filtering viruses in a monoclonal antibody solution using a virus-removing membrane, wherein (1) the monomer content of the monoclonal antibody accounts for 90% or more;
(2) the monoclonal antibody concentration in the monoclonal antibody solution ranges from 20 mg/ml to 100 mg/ml;
(3) the monoclonal antibody solution contains at least a basic amino acid; and
(4) the parvovirus removal rate of the virus-removing membrane satisfies the following conditions:
LRV (Log Reduction Value: logarithmic reduction value)≥4.

18 Claims, No Drawings

METHOD FOR REMOVING VIRUSES FROM HIGH CONCENTRATION MONOCLONAL ANTIBODY SOLUTION

TECHNICAL FIELD

The present invention relates to a method for removing viruses existing in a high concentration monoclonal antibody solution and a method for producing a high concentration monoclonal antibody solution.

BACKGROUND ART

Viral inactivation or removal is required for the production process of an antibody drug containing a monoclonal antibody produced by cell culture, because of concerns about contamination with viruses from raw materials or production steps. As a method for inactivation of viruses that may contaminate an antibody drug, heat treatment, treatment using a chemical agent or the like is performed. However, viruses cannot be sufficiently inactivated by such treatment alone. Also, these methods may directly denature the antibody in the antibody drug. Starting from this background, viral separation and removal using filter membranes are performed as a physical means for removing viruses without chemical denaturation.

As filter membranes for viral removal, a membrane comprising natural material such as cellulose and a virus-removing membrane comprising a synthetic polymer material such as polyvinylidene fluoride (PVDF) or polyether sulfone (PES) are known (Non-Patent Documents 1-4).

Ideally, a larger amount of an antibody can be filtered within a short time and viruses can be removed with sufficiently high virus removal performance through the filtration of an antibody drug using a virus removal device that includes the above virus-removing membrane. However, in actuality, a cellulose membrane is problematic in that it tends to become clogged even at an antibody concentrations of 20 mg/ml or higher, exhibits low pressure resistance, and can increase actual working pressure to only about 100 kPa, although filtration is possible, for example. Alternatively, a synthetic polymer membrane may have high pressure resistance and may function without problems even if the actual working pressure is increased to about 300 kPa. However, the synthetic polymer membrane is problematic in that it becomes clogged when the antibody concentration is increased to about 20 mg/ml, making filtration impossible to perform. Hence, filtration is generally performed at low concentrations of 10 mg/ml or lower.

However, in recent years, the pharmaceutical concentrations of antibody drugs have been on the increase. Reflecting the trend, the demand for an increase in antibody concentration during the filtration step for removing viruses is increasing. When the antibody concentration in a monoclonal antibody solution is increased, monoclonal antibodies tend to become associated with each other so as to form aggregates. When filtration is performed using a membrane having a small pore diameter, as in the case of a virus-removing membrane, association of monoclonal antibodies with each other becomes further significant because of physical stresses resulting from filtration, and thus the virus-removing membrane becomes clogged as described above.

In particular, in order to remove a small virus having a diameter of about 18-24 nm such as a parvovirus from a monoclonal antibody solution at a high removal rate, a virus-removing membrane with a small pore diameter intended for the removal of parvoviruses is required. Such a membrane is problematic in that it becomes easily clogged when a high concentration monoclonal antibody solution is filtered, the resulting antibody recovery rate is disadvantageously low, and a very long time is required for filtration.

There is a prior art reference that does not disclose any monoclonal antibody, but discloses a method for removing viruses from a protein solution by nanofiltration. Specifically, the method targeting fibrinogen comprises: adding at least one ingredient that is selected from a chaotropic substance selected from arginine, guanidine, citrulline, urea, a derivative thereof, and a salt thereof, and a compound selected from polyethoxy sorbitan ester and a derivative thereof, to a protein solution; and then filtering the protein solution using a virus-removing membrane having a pore diameter that is 15 nm or more and less than 35 nm (Patent Document 1).

Patent document 1 discloses the assumption that the ingredient may suppress or inhibit the association of protein molecules or hydrated layer formation in the vicinity of molecules. However, intended proteins herein are blood coagulation factors such as fibrinogen and VIII factor. Also, in examples in Patent Document 1, the membrane permeability of a fibrinogen solution in the presence of arginine is merely compared with the same in the absence of arginine. Furthermore, the fibrinogen concentration is less than 5 mg/ml and the subject is a low-concentration solution. Fibrinogen is a long, slender, thread-shaped protein having a length of nearly 60 nm, which is polymerized upon bleeding and thus is useful for hemostasis. On the other hand, a monoclonal antibody is a spherical protein having a diameter of about 15 nm and having physicochemical properties (e.g., isoelectric point and hydrophilicity) that differ significantly from those of fibrinogen. Patent Document 1 is an invention relating to fibrinogen. Moreover, the invention of Patent Document 1 is not a technology relating to monoclonal antibodies, but a technology relating to fibrinogen as a protein having properties completely differing from those of monoclonal antibodies. Thus, Patent Document 1 is not a good reference for the purification of monoclonal antibodies.

Patent Document 2 describes a method for removing viruses from a fibrinogen-containing solution that may contain viruses by using a virus-removing membrane, which is characterized in that the solution containing fibrinogen contains basic amino acid or salts thereof and sodium chloride. Patent Document 2 also relates to viral removal using a membrane wherein a fibrinogen solution is used. Moreover, the protein concentration in Patent Document 2 ranges from as low as 5 mg/ml to 16.5 mg/ml, significantly differing from the high concentration monoclonal antibody solution that is an object of the present application. Furthermore, the virus-removing membrane used in Patent Document 2 is a membrane with low ability to remove small viruses such as parvoviruses, and it allows small viruses to pass through it. The sizes of viruses to be removed by the invention of Patent Document 2 are larger than those of the subject viruses of the present application. Hence, the technology of Patent Document 2 poses no problem upon filtration concerning the relationship between aggregates of monoclonal antibodies and the membrane.

Solution conditions (e.g., pH and ionic strength) when a virus-removing membrane is used in a purification process for a monoclonal antibody, are varied. Accordingly, the physicochemical properties of the antibody surface and the membrane surface differ depending on solution conditions. Actually, there has been a case in which the flux was very low upon antibody filtration depending on solution conditions. The interaction between the antibody surface and the membrane surface is one reason for such a low flux, and in particular, electrostatic interaction that functions between the two affects such a low flux. The electric charge property of the antibody surface and the membrane surface is expressed as surface potential (zeta potential) that is changed to a positive or negative potential state depending on the relationship between the solution pH and isoelectric point (pI). It is known that pI of a monoclonal antibody ranges from 6 to 10. When pH<pI, a monoclonal antibody has high positive potential and acts adversely in membrane filtration. Therefore, it is thought that if the surface potential of an antibody is lowered and its electrostatic interaction with the membrane is suppressed, the flux during filtration will be improved. Meanwhile, under such solution conditions, a high concentration monoclonal antibody solution is problematic in that dispersion stability becomes poor because of the antibodies' own charges, antibodies tend to form aggregates, and thus the flux decreases over time during membrane filtration.

Specifically, there has been no prior art concerning a method for removing even small viruses using a membrane within a short time at high yield from a high concentration monoclonal antibody solution through the control of the surface potentials of the membrane and antibodies and the suppression of the association of antibodies (contained in a solution at a high concentration) with each other, so as to improve the filterability of the membrane.

PRIOR ART DOCUMENTS

Patent Documents

Patent Document 1: U.S. Patent Publication No. 2003/0232969
Patent Document 2: JP Patent Publication (Kokai) No. 2001-335509

Non-Patent Documents

Non-Patent Document 1: Manabe. S, Removal of virus through novel membrane filtration method., Dev. Biol. Stand., (1996) 88: 81-90.
Non-Patent Document 2: Brandwein H et al., Membrane filtration for virus removal., Dev Biol (Basel)., (2000) 102: 157-63.
Non-Patent Document 3: Aranha-Creado et al., Clearance of murine leukaemia virus from monoclonal antibody solution by a hydrophilic PVDF microporous membrane filter., Biologicals. (1998) June; 26 (2): 167-72.
Non-Patent Document 4: Mocé-Llivina et al., Comparison of polyvinylidene fluoride and polyether sulfone membranes in filtering viral suspensions, Journal of Virological Methods, (2003) April, Vol. 109, Issue 1, Pages 99-101.

SUMMARY OF THE INVENTION

Object to be Solved by the Invention

In view of the above problems, an object of the present invention is to provide a method for removing even small viruses from a high concentration monoclonal antibody solution using a membrane, and thus for recovering the antibody within a short time at high yield in the form of a filtrate.

Means for Solving the Object

As a result of intensive studies to address the above problems, the present inventors have discovered that viruses existing in a high concentration monoclonal antibody solution can be removed at a high removal rate through filtration with a virus-removing membrane using a monoclonal antibody solution supplemented with a basic amino acid. Thus, the present inventors have completed the present invention. Specifically, the following invention is provided according to the present invention.

[1] A method for producing a preparation containing a monoclonal antibody, which comprises a step of removing viruses by filtering viruses in a monoclonal antibody solution using a virus-removing membrane, wherein
(1) the monomer content of the monoclonal antibody accounts for 90% or more;
(2) the monoclonal antibody concentration in the monoclonal antibody solution ranges from 20 mg/ml to 100 mg/ml;
(3) the monoclonal antibody solution contains at least a basic amino acid; and
(4) the parvovirus removal rate of the virus-removing membrane satisfies the following conditions:
LRV (Log Reduction Value: logarithmic reduction value)≥4.

[2] A method for removing viruses in a monoclonal antibody solution, which comprises a step of removing viruses by filtering viruses in a monoclonal antibody solution using a virus-removing membrane, wherein
(1) the monomer content of the monoclonal antibody accounts for 90% or more;
(2) the monoclonal antibody concentration in the monoclonal antibody solution ranges from 20 mg/ml to 100 mg/ml;
(3) the monoclonal antibody solution contains at least a basic amino acid; and
(4) the parvovirus removal rate of the virus-removing membrane satisfies the following conditions:
LRV (Log Reduction Value: logarithmic reduction value)≥4.

[3] A method for producing a preparation containing a monoclonal antibody, which comprises a step of removing viruses by filtering viruses in a monoclonal antibody solution using a virus-removing membrane, wherein
(1) the monomer content of the monoclonal antibody accounts for 90% or more;
(2) the monoclonal antibody concentration in the monoclonal antibody solution ranges from 20 mg/ml to 100 mg/ml;
(3) the monoclonal antibody solution contains at least a basic amino acid; and
(4) the zeta potential $Ei1$ (mV) of the monoclonal antibody in the solution satisfies the following conditions:
a) $0\ mV \leq Ei1-Em \leq 20\ mV$, with respect to the zeta potential $Em$ (mV) of the virus-removing membrane; and satisfies the following conditions:
b) $10\ mV \leq Ei0-Ei1 \leq 40\ mV$, with respect to the zeta potential $Ei0$ (mV) of the monoclonal antibody in the solution (pH=4 and ionic strength of 0.1 mM) containing the monoclonal antibody.

[4] A method for removing viruses by filtering a monoclonal antibody solution containing a monoclonal antibody using a virus-removing membrane, wherein:
(1) the monomer content of the monoclonal antibody accounts for 90% or more;
(2) the monoclonal antibody concentration in the monoclonal antibody solution ranges from 20 mg/ml to 100 mg/ml;
(3) the monoclonal antibody solution contains at least a basic amino acid; and
(4) the zeta potential $Ei1$ (mV) of the monoclonal antibody in the solution satisfies the following conditions:
a) $0\ mV \leq Ei1-Em \leq 20\ mV$, with respect to the zeta potential $Em$ (mV) of the virus-removing membrane; and satisfies the following conditions:

b) 10 mV≤Ei0−Ei1≤40 mV, with respect to the zeta potential Ei0 (mV) of the monoclonal antibody in a solution (pH=4 and ionic strength of 0.1 mM) containing the monoclonal antibody.

[5] The method according to [3] or [4], wherein the zeta potential Ei1 (mV) of the monoclonal antibody in the monoclonal antibody solution satisfies the following conditions: −4%×Em≤Ei1≤−550%×Em, with respect to the zeta potential Em (mV) of the virus-removing membrane.

[6] The method according to any one of [3] to [5], wherein the zeta potential Ei0 (mV) of the monoclonal antibody contained in a solution (pH=4 and ionic strength of 0.1 mM) containing the monoclonal antibody is +25 mV or higher.

[7] The method according to any one of [1] to [6], wherein the monoclonal antibody solution is prepared by cell culture.

[8] The method according to any one of [1] to [7], wherein the pH of the monoclonal antibody solution ranges from 4 to 7.

[9] The method according to any one of [1] to [8], wherein the material of the virus-removing membrane is cellulose.

[10] The method according to any one of [1] to [9], wherein the material of the virus-removing membrane is a hydrophilized synthetic polymer.

[11] The method according to [10], wherein the synthetic polymer is polyvinylidene fluoride, polyether sulfone, polysulfone, or polyethylene.

[12] The method according to any one of [1] to [11], wherein the basic amino acid is arginine, histidine, lysine or a derivative thereof, or a salt thereof.

[13] The method according to any one of [1] to [12], wherein the basic amino acid content in the monoclonal antibody solution ranges from 0.1 mmol/g to 20 mmol/g with respect to the antibody.

[14] The method according to any one of [1] to [13], wherein the antibody throughput is 2 kg/m$^2$/3 hours/bar (based on pressure) or more.

[15] The method according to any one of [1] to [14], wherein the monoclonal antibody solution contains one or more types of member selected from among an inorganic salt, a buffer ingredient, a surfactant, and a saccharide.

[16] The method according to any one of [1] to [15], wherein filtration using the virus-removing membrane is dead-end filtration.

[17] The method according to any one of [1] to [16], wherein the step of removing viruses by filtering a monoclonal antibody solution using a virus-removing membrane is performed after chromatography, concentration, or buffer exchange.

[18] The method according to any one of [1] to [17], wherein the step of removing viruses by filtering a monoclonal antibody solution using a virus-removing membrane is performed after concentration or buffer exchange.

Effect of the Invention

According to the present invention, both suppression of the aggregate formation by antibodies and control of the relationship between the potential of the antibodies and that of the membrane become possible, a high concentration monoclonal antibody solution can be treated within a short time at high yield, and even small viruses can be removed at high removal rates. According to the present invention, additional effects can be expected such that antibody drug production step can be simplified, the step can be more compact, and the cost of the step can be reduced.

EMBODIMENTS FOR CARRYING OUT THE INVENTION

Hereinafter, the present invention will be described in detail.

Antibodies to be used in the present invention are monoclonal antibodies. Also, monoclonal antibodies may be produced or purified by any method. Antibodies to be used in the present invention are preferably monoclonal antibodies that are prepared by culturing animal cells such as CHO. Basically, any known techniques can be used for production of monoclonal antibodies. An animal is immunized with an antigen according to a general immunization method, cells producing monoclonal antibodies are screened by a known screening method, hybridomas of these cells with tumor cells are prepared, hybridomas are cultured in large scale, so that the monoclonal antibodies can be prepared.

Furthermore, monoclonal antibodies to be used herein are not limited to (mouse) monoclonal antibodies produced by hybridomas. Examples of monoclonal antibodies to be used herein include chimeric antibodies artificially altered for the purpose of lowering the antigenicity of heteroantibody against a human, or the like. Alternatively, a reconstructed humanized antibody can also be used for the present invention. Such a reconstructed humanized antibody is prepared by substituting a complementarity determining region of a human antibody with the same of an antibody of a non-human mammal such as mouse. General gene recombination techniques therefor are also known. A reconstructed humanized antibody can be obtained by such a known method.

The concentration of an antibody in a monoclonal antibody solution ranges from 20 mg/ml to 100 mg/ml, preferably ranges from 20 mg/ml to 80 mg/ml, more preferably ranges from 20 mg/ml to 70 mg/ml, and further more preferably ranges from 20 mg/ml to 50 mg/ml. When the concentration of an antibody increases, the filtration rate by a virus-removing membrane tends to decrease.

Antibody purity in a monoclonal antibody solution is 90% or more (monomer) and is more preferably 95% or more. Impurities other than monomers contained in an antibody solution are associates and aggregates that are dimers, trimers, tetramers, or multimers greater than tetramers of antibodies. When the amounts of associates or aggregates are high, a virus-removing membrane becomes clogged upon filtration, and thus high throughput cannot be obtained.

A monoclonal antibody solution contains at least a basic amino acid. As a basic amino acid, arginine, histidine, guanidine, lysine or a derivative thereof, or a salt thereof can be used. A basic amino acid is preferably arginine, histidine, lysine, or a derivative thereof, or a salt thereof. A basic amino acid is more preferably arginine or a derivative thereof, or a salt thereof.

The concentration of a basic amino acid in a monoclonal antibody solution preferably ranges from 10 mM to 300 mM in view of the effect of improving filterability. Also, the content of a basic amino acid (with respect to antibodies) in a monoclonal antibody solution preferably ranges from 0.1 mmol/g to 20 mmol/g, more preferably ranges from 0.3 mmol/g to 10 mmol/g, and further more preferably ranges from 0.6 mmol/g to 7 mmol/g, in view of the effect of improving filterability.

(Action Principle of Basic Amino Acid)

The reason why the filterability is improved through addition of a basic amino acid to a monoclonal antibody solution remains unrevealed. The present inventors consider as follows. It is known that an antibody is generally (+) charged at an isoelectric point or lower. A basic amino acid in the present invention is thought to have the effect of decreasing the potential of the antibody surface and thus suppressing electrostatic interaction (electrostatic attraction) with the (−) charge of the virus-removing membrane. Also, in general, within the pH range near the isoelectric point of antibodies, antibodies tend to associate with each other through hydrophobic interaction since electrostatic repulsion between antibodies decreases; or filterability tends to decrease because of hydrophobic interaction between antibodies and the membrane. It is considered that a basic amino acid also has an effect of suppressing antibody-antibody hydrophobic interaction and antibody-membrane hydrophobic interaction.

The surface potential of antibodies or a membrane is expressed as zeta potential. Regarding a method for measuring the surface zeta potential of antibodies or a membrane, the surface zeta potential can be measured by an electrophoresis light scattering method using an ELS-Z zeta potential analyzer (Otsuka Electronics Co., Ltd.), for example, but the measurement method is not limited thereto. When the zeta potential of monoclonal antibodies under given solution conditions is designated as $Ei1$ (mV) and the zeta potential of a virus-removing membrane under given solution conditions is designated as $Em$ (mV), the two desirably have the following relationship. Here, the term "the zeta potential of a virus-removing membrane under given solution conditions" refers to "the zeta potential of the relevant virus-removing membrane under conditions in which the virus-removing membrane is filled with a solution having the same composition as that of a monoclonal antibody solution but containing no monoclonal antibodies".

The relationship between the zeta potential $Ei1$ of antibodies and the zeta potential $Em$ of a membrane is desirably represented by $$0 \text{ mV} \leq Ei1 - Em \leq 20 \text{ mV}.$$

When the result of $Ei1-Em$ is within the range that allows interaction between the antibodies and the membrane to decrease, it is thought to have an effect of improving the filtration rate of the membrane. A value for $Ei1-Em$ of more than 20 mV causes electrostatic interaction between antibodies and the membrane to increase, having an adverse effect on filtration.

Also, regarding the potential of the virus-removing membrane of the present invention, the virus-removing membrane is negatively charged within the pH range of the present application. Furthermore, antibodies are positively charged. To express it in another way, the relationship between the zeta potential $Ei1$ of antibodies and the zeta potential $Em$ of a membrane is desirably represented by $$-4\% \times Em \leq Ei1 \leq -550\% \times Em.$$

In the case of the monoclonal antibodies of the present invention, the zeta potential (basic potential) of the antibodies, $Ei0$ (mV), under the pH at or below the isoelectric point of antibodies, specifically, pH=4, and ionic strength of 0.1 mM, is desirably +25 mV or higher. Specifically, the zeta potential is preferably +27 mV or higher and is more preferably +29 mV or higher.

To suppress electrostatic interaction between antibodies and a membrane and thus to enable expression of high filterability (Flux) through the addition of a basic amino acid, the surface potential (zeta potential) $Ei1$ of the antibodies is desirably decreased to +20 mV or lower.

Furthermore, the relationship between the zeta potential of antibodies $Ei0$ and $Ei1$ is desirably represented by $$10 \text{ mV} \leq Ei0 - Ei1 \leq 40 \text{ mV}.$$

When the result of $Ei0-Ei1$ is lower than 10 mV, the effect of decreasing the basic potential of the antibodies is weak, and thus the expected effect of improving the filtration rate cannot be obtained.

The pH of a monoclonal antibody solution preferably ranges from 4.0 to 7.0. When the pH is less than 4.0 or more than 7.0, antibodies themselves can be denatured or degraded. Within the pH ranging from 4.0 to 7.0, antibodies themselves are stable and the surface thereof are + charged, so that aggregate formation is suppressed. Also, a basic amino acid exhibits an effect of improving filterability within the pH range between 4.0 and 7.0 upon filtration of antibodies (contained in a solution at a high concentration) using a virus-removing membrane.

A monoclonal antibody solution may further contain one or more types of member selected from inorganic salts, buffer ingredients, surfactants, and saccharides.

The monoclonal antibody solution can contain NaCl, a buffer salt, or the like as an inorganic salt. As a buffer, an acetate buffer, a citrate buffer, a phosphate buffer, a Tris-HCl buffer, or the like can be used. The concentration of an inorganic salt or the concentration of a buffer ingredient preferably ranges from 10 mM to 500 mM in terms of ionic strength. Here, ionic strength can be calculated by the following formula.

$$\text{Ionic strength} = \tfrac{1}{2} \times \Sigma (Ci \times Zi^2)$$

$Ci$; molarity, $Zi$; ionic valence

As a surfactant, a nonionic surfactant such as Tween20 or Tween80 can be used. The concentration of such a surfactant that can be contained ranges from 0.01 w % to 0.05 w %.

As a saccharide (e.g., a monosaccharide, a disaccharide, a trisaccharide, an oligosaccharide, or sugar alcohol) that is an additive, glucose, mannose, galactose, fructose, sorbose, maltose, sucrose (saccharose), sorbitol, mannitol, dextran, or the like can be contained in an amount ranging from 1 w % to 10 w % and preferably ranging from 1 w % to 5 wt %.

As material for a virus-removing membrane, cellulose or a hydrophilized synthetic polymer can be used. As cellulose, regenerated cellulose, natural cellulose, acetic acid cellulose, and the like can be used. As a hydrophilized synthetic polymer, hydrophilized polyvinylidene fluoride (PVDF), hydrophilized polyether sulfone (PES), hydrophilized polyethylene (PE), hydrophilized polysulfone (PS), or the like can be used. An example of a hydrophilization method is a method for introducing a hydrophilic functional group to or fixing a hydrophilic polymer to the surface of a membrane via coating, graft reaction, crosslinking reaction, or the like.

Regarding the shape of a membrane, either a flat membrane or a hollow fiber membrane can be used. When the area of a membrane is large, a small filter (prepared by loading a container with the membrane) can be employed. Hence, the membrane used herein is preferably a hollow fiber membrane. A filter in which the space is partitioned by a membrane into a primary space on the inlet side for a solution to be filtered and a secondary space on the outlet side for the filtered solution can be prepared. When a virus-removing membrane is used for filtration, it can be used in the form of the filter.

A virus-removing membrane is required to have parvovirus removal performance of LRV4 or more and more desirably LRV5 or more. Examples of commercially available virus removal filters for removing parvoviruses, include Planova™ 15N (Asahi Kasei Medical) and Planova™ 20N (Asahi Kasei Medical), wherein a virus-removing membrane comprises cellulose, and Virosart CPV (Sartorius) and Viresolve Pro (Millipore) that comprise hydrophilized PES.

There is an actual case concerning parvoviruses such that monoclonal antibodies are contaminated therewith in a production process as a result of contamination of CHO cells (mouse-derived) with a mouse parvovirus. Viral safety evaluation guidelines (ICH Q5A) for biological pharmaceutical products produced using animal cells have been issued by the FDA.

Parvoviruses have no envelope, so that they are physically and chemically stable. Hence, parvoviruses are resistant to heating, low pH, and treatment with a chemical agent, which are generally performed during an inactivation step of the production process for a biological preparation. Thus, there is a growing need for a method for removing parvoviruses using a virus-removing membrane as a method for removing viruses, having a mode of action that differs from that of an inactivation method.

Parvoviruses belong to the family *Parvoviridae*, and they are currently known to be some of the smallest viruses (18-24 nm in diameter). Examples of parvoviruses include mouse parvovirus (MVM), porcine parvovirus (PPV), and canine parvovirus (CPV). For evaluation of the virus-removing membrane of the present application, PPV is used as a model virus.

The virus removal performance of a virus-removing membrane is represented by LRV (Log Reduction Value).

LRV is obtained by calculating the change in viral concentration in an antibody solution between before and after filtration with the virus-removing membrane by the following formula.

$$LRV = \log_{10}(C_O/C_F)$$

wherein $C_O$=viral concentration in an antibody solution before filtration with the virus-removing membrane, and $C_F$=viral concentration in the antibody solution after filtration with the virus-removing membrane Viral concentration can be expressed with infectivity titer, the number of viral nucleic acid copies, and the like. Examples of a method for measuring infectivity titer include a TCID50 method and a plaque method. The number of viral nucleic acid copies can be measured by a PCR method or the like.

Before filtration with a virus-removing membrane, the concentration of monoclonal antibodies should be adjusted to range from 20 mg/ml to 100 mg/ml and the composition of the antibody solution should be adjusted to at least contain a basic amino acid. As described above, the pH of a monoclonal antibody solution preferably ranges from 4 to 7. The concentration of a basic amino acid preferably ranges from 0.1 mmol/g to 20 mmol/g per antibody.

A basic amino acid is added to an antibody eluate to reach a given concentration after treatment with chromatography, so as to be able to adjust the pH as given. Alternatively, buffer exchange can also be performed by a known method so that the buffer composition of the eluate is exchanged with the composition of a solution adjusted to have given concentration of a basic amino acid and pH. Also, antibody concentration and buffer exchange are simultaneously performed, so that the solution composition can also be adjusted as desired. pH adjustment can be performed using NaOH, HCl, inorganic acid, organic acid, and buffer. As a buffer, an acetate buffer, a citrate buffer, a phosphate buffer, or the like can be used.

A filtration method for an antibody solution using a virus-removing membrane is preferably performed by dead-end filtration. Specifically, either constant pressure filtration using constant filtration pressure or constant velocity filtration using constant filtration velocity may be employed. Filtration is performed with filtration pressure that is the same as or below the level at which the membrane can withstand, depending on the material of a virus-removing membrane to be used herein. For example, in the case of a virus-removing membrane comprising cellulose, the optimum pressure ranges from 49 kPa (0.5 bar) to 98 kPa (1 bar). In the cases of hydrophilized PVDF, hydrophilized PES, and hydrophilized PS, the optimum pressure ranges from 98 kPa (1 bar) to 490 kPa (5 bar).

The temperature for filtration with a virus-removing membrane may be within any temperature range, as long as it has no effect on the state of an antibody solution (the antibody is not denatured). Preferably the temperature ranges from 4° C. to 40° C. and more preferably ranges from 4° C. to 35° C. The temperature has an effect on the viscosity of an antibody solution and also has an effect on the flux upon filtration with a virus-removing membrane. Thus, the temperature further preferably ranges from 20° C. to 35° C., depending on the antibody's own stability to temperature.

After adjustment of a solution to have a given composition and before filtration with a virus-removing membrane, pre-filtration can also be performed with a filter comprising a membrane with a pore diameter larger than that of the virus-removing membrane. Here, as such a filter with a larger pore diameter, Planova™35N, Planova™75N (these are produced by Asahi Kasei Medical), a 0.1 μm filter, a 0.2 μm filter, or the like can be used. Without prefiltration, filtration can also be directly performed using a virus-removing membrane.

In general, antibody throughput (the amount of an antibody treated) of 2 kg/m²/3 hours/bar (or 98 kPa) is obtained per virus-removing membrane area, time, and filtration pressure within the above-mentioned antibody concentration, filtration pressure, and temperature ranges. Antibody throughput is calculated from the volume (V) of filtrate per unit above and the concentration (C) of antibodies collected in the filtrate (antibody throughput=V×C). Both filterability and yield can be evaluated on the basis of the throughput.

(Position for Viral Filtration in Downstream)

A step of filtration with a virus-removing membrane is performed after chromatography, after concentration, or after concentration/buffer exchange. Examples of chromatography include column chromatography using a column filled with an ion exchange resin or a gel-filtration resin and membrane chromatography using a porous membrane on the surface of which an ion exchange group has been provided. Examples of separation modes for chromatography include gel filtration chromatography, ion exchange chromatography (cation exchange; CEX or anion exchange; AEX), hydrophobic interaction chromatography (HIC), affinity chromatography, metal chelate affinity chromatography, and hydroxy apatite chromatography. An example of chromatography using a ligand is chromatography using ion exchange and hydrophobic interaction in combination.

An concentration step can be performed according to a known method using an ultrafiltration (UF) membrane. Specifically, the step can be performed by centrifugal concentration.

A buffer exchange step can also be performed according to a known method. Specifically the buffer exchange step can be performed simultaneously with concentration using an ultrafilter membrane. The buffer exchange step can also be performed by a gel filtration method. The buffer exchange step can also be performed by a dialysis method using a dialysis membrane.

Subsequent to filtration using a virus-removing membrane, purification treatment can also be performed by chromatography treatment. Also, even higher concentration can be achieved by UF treatment. Final formulation can also be performed using the same solution composition as that upon filtration with a virus-removing membrane. Also, a saccharide, a surfactant, or the like is added after filtration with a virus-removing membrane and then final formulation can also be performed. Buffer exchange with a solvent having another composition is also possible. Lyophilization can further be performed.

EXAMPLES

In the following examples, Planova™20N (Asahi Kasei Medical) (hereinafter, denoted as Filter A) comprising a cellulose hollow fiber membrane as a virus-removing membrane and a filter (hereinafter, denoted as Filter B) comprising a hydrophilized polyvinylidene fluoride hollow fiber membrane as a virus-removing membrane were used.

Also, as an intermediate product model of a monoclonal antibody preparation, a monoclonal antibody solution was prepared according to the method described in International Patent Publication No. 04/087761 as described below ("Preparation of Monoclonal Antibody") and then used.
(Preparation of Filter B)

A composition comprising 49 wt % polyvinylidene fluoride resin (Kureha Corporation, T#1300) with a melt flow index (MFI) of 2.5 (g/10 ml) and 51 wt % dicyclohexyl phthalate (Osaka Organic Chemical Industry Ltd., industry product) was stirred and mixed at 70° C. using a henschel mixer (Mitsui Mining Co., Ltd.; format: 20B), cooled, and then pulverized. The resultant was applied using a hopper to a co-rotating twin screw extruder (Technovel Corporation, KZW25TW-50MG-NH (−600)), melted and mixed at 210° C., and then homogeneously dissolved. Subsequently, homogenously dissolved products were each extruded in the form of hollow fiber from a spinning orifice comprising a ring orifice (inner diameter: 0.8 mm; outer diameter: 1.05 mm) while dibutyl phthalate (Daihachi Chemical Industry Co., Ltd., industry product) was injected at 130° C. into the hollow interior. The products were cooled and solidified in cooling water regulated at a temperature of 10° C., 20° C., 30° C., or 40° C., and then wound around a metal frame at a speed of 50 m/minute. Subsequently, dicyclohexyl phthalate and dibutyl phthalate were extracted and removed with a 58 wt % aqueous isopropylalcohol solution (Daihachi Chemical Industry Co., Ltd., industry product). the attached 58 wt % aqueous isopropylalcohol solution was substituted with water. The resultant was immersed in water and then heated at 125° C. using an autoclave (Hirayama Manufacturing Corporation, HV-85) for 4 hours. The attached water was substituted with isopropylalcohol (Daihachi Chemical Industry Co., Ltd., industry product) and then the resultant was dried using a vacuum drier (Stec Co., Ltd.) at a temperature of 60° C., so that a hollow fiber microporous membrane was obtained. In all steps from winding to drying, treatment was performed while the lengths of hollow fibers remained fixed.

Subsequently, hydrophilization treatment was performed by a graft method for the above microporous membrane. The reaction solution used herein was prepared by dissolving hydroxypropyl acrylate (Osaka Organic Chemical Industry Ltd., industry product) in a 25 vol % aqueous solution of 3-butanol (Junsei Chemical Co., Ltd., industry product) so as to achieve 8 vol % hydroxypropyl acrylate, and then performing nitrogen bubbling for 30 minutes while keeping it at 45° C. First, under a nitrogen atmosphere, the microporous membrane was irradiated with 25 kGy of γ-ray using Co60 as a radiation source while cooling it with dry ice at −60° C. The thus irradiated microporous membrane was left to stand for 15 minutes under reduced pressure of 13.4 Pa or less. The above reaction solution and the microporous membrane were brought into contact with each other at 60° C. and then left to stand for 1 hour. Thereafter, the microporous membrane was washed with a 58 wt % aqueous isopropylalcohol solution and then subjected to 4 hours of vacuum drying at 60° C. Thus, a hydrophilic microporous membrane was obtained. It was confirmed that water spontaneously infiltrated the pores when the microporous membrane was brought into contact with water. Both ends of a bundle of 12 microporous membranes were sealed with polyurethane. The bundle was connected to a cartridge wherein the hollow fiber membranes made of polystyrene were partitioned into a space on the inlet side and a space on the outlet side, so that a filter (effective membrane area: 0.001 $m^2$) was prepared. The filter obtained by the above method comprising the hydrophilized PVDF hollow fiber membranes is hereinafter denoted as Filter B.
(Preparation of Monoclonal Antibody)

A CHO cell serum free culture supernatant (1500 ml) (expression level: 700 mg/L) containing a human monoclonal antibody (human IgG1) clarified with a depth filter and a 0.2-μm membrane filter was added (linear velocity: 500 cm/h) to a Protein A column (GE Healthcare Bioscience, Mabselect 20 mm ID×20 cm) that had been equilibrated with 10 (mmol/l) sodium phosphate buffer (pH 6.0). Next, the human monoclonal antibody was eluted (linear velocity: 500 cm/h) using 5 column volumes of 20 mmol/l sodium citrate buffer (pH 3.4). The eluate was neutralized with 10 mmol/l sodium phosphate buffer (pH 8.2), adjusted to pH 8.0 using 1.5 (mmol/l) Tris-HCl and then added (linear velocity: 300 cm/h) to an anion exchange column (GE Healthcare Bioscience, Q Sepharose XL 10 mm ID×15 cm) that had been equilibrated with 10 mmol/l Tris-HCl After completion of addition, 3 column volumes of equilibration buffer were applied to a column (linear velocity: 300 cm/h). The fraction not adsorbed to the column was adjusted to pH 5.0 with 1.0 mol/l acetic acid and then the resultant was added (linear velocity: 300 cm/h) to a cation exchange column (GE Healthcare Bioscience, SP Sepharose FF, 26 mm ID×15 cm) that had been equilibrated with 20 mmol/l sodium acetate buffer (pH 5.0). After completion of addition, the resultant was washed with 5 column volumes of equilibration buffer (linear velocity: 300 cm/h), and then 5 column volumes of 20 mmol/l sodium acetate/0.30 (mol/l) sodium chloride buffer (pH 5.0) were further applied, so that a human monoclonal antibody solution was eluted (linear velocity: 300 cm/h). The eluate was subjected to concentration and buffer composition exchange using an ultrafilter membrane (Millipore, Biomax-30; 50 $cm^2$) so that the following solution conditions (as shown in Table 1 and Table 2 below) were satisfied.
(Measurement of Virus Removal Performance)

Cultured PK-13 cells (obtained from ATCC; ATCC No. CRL-6489) were diluted with D-MEM (Invitrogen Corporation, high-glucose) (the mixture is hereinafter referred to as "3% FBS/D-MEM") supplemented with 3 vol % bovine serum (Upstate, heated in water at 56° C. for 30 minutes for inactivation and then used) and 1 vol % penicillin/streptomycin (+10000 Units/ml Penicillin, +10000 μg/ml Streptomycin, Invitrogen Corporation). Thus, a diluted suspension with a cell concentration of 2.0×$10^5$ cells/ml was prepared. The cell suspension was dispensed at 100 μl each to all wells of ten 96-well round bottom cell culture plates (Falcon) that had been prepared.

Subsequently, the total amounts of the mixtures of filtrates subjected to 3 hours of filtration were diluted 10-fold, $10^2$-fold, $10^3$-fold, $10^4$-fold, and $10^5$-fold with 3% FBS/D-MEM, thereby preparing diluents. Moreover, each original solution collected immediately before filtration was diluted $10^2$-fold, $10^3$-fold, $10^4$-fold, $10^5$-fold, $10^6$-fold, and $10^7$-fold with 3% FBS/D-MEM, therby preparing diluents. To the 96-well cell culture plates into which the above cell suspension had been dispensed, each filtrate, 10-fold, $10^2$-fold, $10^3$-fold, $10^4$-fold, and $10^5$-fold diluents prepared from the filtrate, and $10^2$-fold, $10^3$-fold, $10^4$-fold, $10^5$-fold, $10^6$-fold, and $10^7$-fold diluents prepared from the original solution were dispensed at 100 (μl) per 8 wells, followed by 10 days of culture at 37° C. under a 5% carbon dioxide atmosphere within an incubator.

Next, the above cell culture plates were subjected after 10 days of culture to measurement of TCID50 (50% infectivity titer) by an erythrocyte adsorption method (*Virus Jikken Gaku* (Experimental Study of Viruses), General, Ed., National Institute of Infectious Diseases, p. 173). Conserved blood of chicken (Nippon Biotest Laboratories Inc.) was diluted 5-fold with PBS(-) (Nissui Pharmaceutical Co., Ltd., prepared by a method according to the information included with the commercial product) and then subjected to 5 minutes of centrifugation at 2500 rpm and 4° C., so that erythrocytes were precipitated. Supernatants were removed by suction. The thus obtained precipitates containing the erythrocytes were again diluted 200-fold with PBS(-).

Next, 100 μl of each PBS(-) diluent of the thus prepared erythrocyte precipitates was dispensed to all wells of the above cell culture plates. After the plates had been left to stand for 2 hours, the presence or the absence of erythrocytes adsorbed to the surfaces of cultured cell tissue was confirmed visually. Wells for which adsorption had been confirmed were determined to be wells in which viral infection had occurred. Wells for which no adsorption had been confirmed were determined to be wells in which no infection had occurred. The numbers of such wells were determined. Regarding the presence or the absence of viral infection in each of the thus obtained culture solutions, the proportion was confirmed for the filtrate, diluents thereof, or diluents of the original solution. Log ($TCID_{50}$/ml) was calculated as an infectivity titer by Reed-Muench method (*Virus Jikken Gaku* (Experimental Study of Viruses), General, Ed., National Institute of Infectious Diseases, p. 479-480). The LRV virus removal rate was found to be LRV4 or more.

(Measurement of Monoclonal Antibody Purity)

Monoclonal antibody solutions were prepared using HPLC (Shimadzu Corporation, Prominence; column: TOSOH Corporation, GPC column, TSK gel G3000SWXL, mobile phase: phosphate buffer (pH 6.9)/0.3 (mol/l) aqueous sodium chloride solution) to satisfy the solution conditions of the following Examples and Comparative examples. The purities of the monoclonal antibody solutions were each measured on the basis of peak area ratio. The results are as shown in Table 3 below.

(Measurement of Zeta Potentials (Surface Potentials) of Antibody and Membrane)

Zeta potential was measured by an electrophoresis light scattering method using an ELS-Z zeta potential analyzer (Otsuka Electronics Co., Ltd.) according to the manufacturer's instructions (Reference: Otsuka Densi Web information, www/photal co. jp.). The zeta potential (Ei1) of antibodies under given solution conditions was calculated on the basis of mobility. The zeta potential (Ei0) of antibodies in a NaCl solution (pH=4, ionic strength: 0.1 mM) was found to be +37 mV. The zeta potential (Em) of membrane was measured using an ELS-Z zeta potential analyzer (Otsuka Electronics Co., Ltd.) similarly to the above according to the manufacturer's instructions. Specifically, the zeta potential (Em) of membrane was measured using cell units for flat-plate samples (Otsuka Electronics Co., Ltd.), the membrane was placed thereon, and then the membrane was filled with a solution having the same composition of the antibody solution but containing no antibody. Under such conditions, zeta potential was measured using monitor particles (Otsuka Electronics Co., Ltd.) coated with hydroxypropyl cellulose and comprising polystyrene latex with almost zero potential (Reference: Otsuka Densi Web information, www/photal co. jp.). In the case of a membrane comprising cellulose, a flat membrane was prepared instead of a hollow fiber membrane (Reference: JP Patent Publication (Kokai) No. 59-45333 A) and then surface zeta potential was measured. The zeta potentials of antibodies and membrane are as shown in Table 4 below.

Examples 1 to 7 and Comparative Examples 1-5

As described above, each monoclonal antibody solution was subjected to concentration and buffer composition exchange so as to satisfy the conditions of Table 1. At this stage, monoclonal antibody purity was measured by the above method. Subsequently, PPV (0.5 vol %) was added and then the resultant was stirred well. The solutions of Examples 1 to 7 and the solutions of Comparative examples 1 to 5 were subjected to 3 hours of dead-end filtration using Filter A having a membrane area of 0.001 $m^2$ under the pressure of 98 kPa (1 bar). The amounts of monoclonal antibodies that could be filtered (kg/$m^2$/3 hr/bar) were calculated and the results are shown in Table 1. PPV removal performance was evaluated by the above method. Furthermore, the results of measuring antibody purity are shown in Table 3.

TABLE 1

| | Additive | Antibody concentration (mg/ml) | Basic amino acid concentration per antibody(mmol/g) | pH | Throughput (kg/$m^2$/3 hours/bar) |
|---|---|---|---|---|---|
| Example 1 | 100 mM arginine | 30 | 3.3 | 4.0 | 2.92 |
| Example 2 | 100 mM arginine | 20 | 5.0 | 4.0 | 2.73 |
| Example 3 | 100 mM histidine | 30 | 3.3 | 4.0 | 2.10 |
| Example 4 | 100 mM arginine | 30 | 3.3 | 5.4 | 2.30 |
| Example 5 | 50 mM arginine | 30 | 1.7 | 5.4 | 2.30 |
| Example 6 | 100 mM arginine | 35 | 2.9 | 5.4 | 2.20 |
| Example 7 | 20 mM histidine 100 mM sodium chloride | 30 | 0.7 | 6.0 | 2.40 |
| Comparative example 1 | 100 mM sodium chloride | 30 | 0 | 4.0 | 1.58 |
| Comparative example 2 | 100 mM sodium chloride | 20 | 0 | 4.0 | 1.83 |
| Comparative example 3 | None | 30 | 0 | 4.0 | 0.75 |

TABLE 1-continued

| | Additive | Antibody concentration (mg/ml) | Basic amino acid concentration per antibody(mmol/g) | pH | Throughput (kg/m²/3 hours/bar) |
|---|---|---|---|---|---|
| Comparative example 4 | 100 mM sodium chloride | 30 | 0 | 5.4 | 1.26 |
| Comparative example 5 | 100 mM sodium chloride | 30 | 0 | 6.0 | 0.70 |

Examples 8-14 and Comparative Examples 6-9

As described above, each monoclonal antibody solution was subjected to concentration and buffer composition exchange, so as to satisfy the conditions of Table 2. At this stage, monoclonal antibody purity was measured by the above method. Thereafter, PPV (0.5 vol %) was added, the resultant was stirred well. The solutions of Examples 8 to 14 and the solutions of Comparative examples 6 to 9 were subjected to 3 hours of dead-end filtration using Filter B having the membrane area of 0.001 m² under the pressure of 294 kPa (3 bar). The amounts of monoclonal antibodies that could be filtered (kg/m²/3 hr/bar) were calculated and the results are shown in Table 2. PPV removal performance was evaluated by the above method. Furthermore, the results of measuring antibody purity are shown in Table 3.

TABLE 2

| | Additive | Antibody concentration (mg/ml) | Basic amino acid concentration per antibody (mmol/g) | pH | Throughput (kg/m²/3 hours/bar) |
|---|---|---|---|---|---|
| Example 8 | 100 mM arginine | 30 | 3.3 | 4.0 | 2.33 |
| Example 9 | 100 mM histidine | 30 | 3.3 | 4.0 | 2.30 |
| Example 10 | 100 mM arginine | 30 | 3.3 | 5.4 | 2.40 |
| Example 11 | 100 mM arginine | 30 | 3.3 | 7.0 | 2.33 |
| Example 12 | 100 mM arginine 100 mM sodium chloride | 30 | 3.3 | 7.0 | 2.42 |
| Example 13 | 100 mM arginine | 50 | 2 | 4.0 | 2.30 |
| Example 14 | 100 mM arginine | 70 | 1.4 | 4.0 | 2.10 |
| Comparative example 6 | 100 mM sodium chloride | 30 | 0 | 4.0 | 1.90 |
| Comparative example 7 | 100 mM sodium chloride | 30 | 0 | 7.0 | 1.67 |
| Comparative example 8 | None | 30 | 0 | 4.0 | 1.45 |
| Comparative example 9 | None | 30 | 0 | 7.0 | 0.43 |

TABLE 3

| | Additive | Antibody concentration (mg/ml) | pH | Antibody purity (%) |
|---|---|---|---|---|
| Examples 1 and 8 | 100 mM arginine | 30 | 4.0 | 96.6 |
| Example 2 | 100 mM arginine | 20 | 4.0 | 97.0 |
| Examples 3 and 9 | 100 mM histidine | 30 | 4.0 | 96.0 |
| Examples 4 and 10 | 100 mM arginine | 30 | 5.4 | 95.0 |
| Example 5 | 50 mM arginine | 30 | 5.4 | 94.0 |
| Example 6 | 100 mM arginine | 35 | 5.4 | 95.0 |
| Example 7 | 20 mM histidine 100 mM sodium chloride | 30 | 6.0 | 95.0 |
| Example 11 | 100 mM arginine | 30 | 7.0 | 93.2 |
| Example 12 | 100 mM arginine 100 mM sodium chloride | 30 | 7.0 | 93.5 |
| Example 13 | 100 mM arginine | 50 | 4.0 | 94.0 |
| Example 14 | 100 mM arginine | 70 | 4.0 | 93.0 |
| Comparative examples 1 and 6 | 100 mM sodium chloride | 30 | 4.0 | 87.8 |
| Comparative example 2 | 100 mM sodium chloride | 20 | 4.0 | 88.0 |
| Comparative examples 3 and 8 | None | 30 | 4.0 | 95.7 |
| Comparative example 4 | 100 mM sodium chloride | 30 | 5.4 | 87.5 |
| Comparative example 5 | 100 mM sodium chloride | 30 | 6.0 | 87.0 |
| Comparative example 7 | 100 mM sodium chloride | 30 | 7.0 | 86.0 |
| Comparative example 9 | None | 30 | 7.0 | 90.6 |

TABLE 4

| | Additive | pH | Zeta potential (Ei1) of antibody (mV) | Zeta otential (Em) of membrane (mV) | Ei1 – Em | Ei0 – Ei1 |
|---|---|---|---|---|---|---|
| Example 1 | 100 mM arginine | 4.0 | +16 | −3 | 19 | 21 |
| Example 3 | 100 mM histidine | 4.0 | +13.2 | −3 | 16.2 | 23.8 |
| Example 4 | 100 mM arginine | 5.4 | +7.3 | −4 | 11.4 | 29.7 |
| Example 7 | 20 mM histidine, 100 mM sodium chloride | 6.0 | +1.4 | −6 | 7.4 | 35.6 |
| Example 8 | 100 mM arginine | 4.0 | +16 | −4 | 20 | 21 |
| Example 10 | 100 mM arginine | 5.4 | +13.3 | −6 | 13.3 | 29.7 |
| Example 11 | 100 mM arginine | 7.0 | +0.6 | −13 | 13.6 | 36.4 |
| Comparative example 1 | 100 mM sodium chloride | 4.0 | +5.8 | −5 | 10.8 | 31.1 |
| Comparative example 3 | None | 4.0 | +37 | −15 | 52 | 0 |
| Comparative example 5 | 100 mM sodium chloride | 6.0 | 0 | −6 | 6 | 31 |
| Comparative example 6 | 100 mM sodium chloride | 4.0 | +5.8 | −4 | 9.8 | 31.1 |
| Comparative example 7 | 100 mM sodium chloride | 7.0 | 0 | −13 | 13 | 37 |
| Comparative example 8 | None | 4.0 | +37 | −13 | 50 | 0 |
| Comparative example 9 | None | 7.0 | +7 | −22 | 29 | 30 |

As a result, monoclonal antibody throughput of 2 kg/m$^2$/3 hr/bar or more could be attained and virus removal performance conditions (PPV LRV 4 or more) could be satisfied in Examples 1 to 14.

INDUSTRIAL APPLICABILITY

The present invention can be used effectively as a method for removing viruses during the production process for an antibody drug.

The invention claimed is:

1. A method for producing a preparation containing a monoclonal antibody, which comprises a step of removing viruses by filtering viruses in a monoclonal antibody solution using a virus-removing membrane, wherein
   (1) the monomer content of the monoclonal antibody accounts for 90% or more;
   (2) the monoclonal antibody concentration in the monoclonal antibody solution ranges from 20 mg/ml to 100 mg/ml;
   (3) the monoclonal antibody solution contains at least a basic amino acid; and
   (4) the parvovirus removal rate of the virus-removing membrane satisfies the following conditions:
   LRV (Log Reduction Value: logarithmic reduction value) ≥4;
   wherein the antibody throughput is 2 kg/m$^{2/3}$ hours/bar (based on pressure) or more; and
   wherein filtration using the virus-removing membrane is dead-end filtration.

2. The method according to claim 1, wherein the monoclonal antibody solution is prepared by cell culture.

3. The method according to claim 1, wherein the pH of the monoclonal antibody solution ranges from 4 to 7.

4. The method according to claim 1, wherein the material of the virus-removing membrane is cellulose.

5. The method according to claim 1, wherein the material of the virus-removing membrane is a hydrophilized synthetic polymer.

6. The method according to claim 5, wherein the synthetic polymer is polyvinylidene fluoride, polyether sulfone, polysulfone, or polyethylene.

7. The method according to claim 1, wherein the basic amino acid is arginine, histidine, lysine or a derivative thereof, or a salt thereof.

8. The method according to claim 1, wherein the basic amino acid content in the monoclonal antibody solution ranges from 0.1 mmol/g to 20 mmol/g with respect to the antibody.

9. The method according to claim 1, wherein the monoclonal antibody solution contains one or more types of member selected from among an inorganic salt, a buffer ingredient, a surfactant, and a saccharide.

10. The method according to claim 1, wherein the step of removing viruses by filtering a monoclonal antibody solution using a virus-removing membrane is performed after chromatography, concentration, or buffer exchange.

11. The method according to claim 1, wherein the step of removing viruses by filtering a monoclonal antibody solution using a virus-removing membrane is performed after concentration or buffer exchange.

12. A method for removing viruses in a monoclonal antibody solution, which comprises a step of removing viruses by filtering viruses in a monoclonal antibody solution using a virus-removing membrane, wherein
   (1) the monomer content of the monoclonal antibody accounts for 90% or more;
   (2) the monoclonal antibody concentration in the monoclonal antibody solution ranges from 20 mg/ml to 100 mg/ml;
   (3) the monoclonal antibody solution contains at least a basic amino acid; and
   (4) the parvovirus removal rate of the virus-removing membrane satisfies the following conditions:
   LRV (Log Reduction Value: logarithmic reduction value) ≥4;
   wherein the antibody throughput is 2 kg/m$^2$/3 hours/bar (based on pressure) or more; and
   wherein filtration using the virus-removing membrane is dead-end filtration.

13. A method for producing a preparation containing a monoclonal antibody, which comprises a step of removing viruses by filtering viruses in a monoclonal antibody solution using a virus-removing membrane, wherein
  (1) the monomer content of the monoclonal antibody accounts for 90% or more;
  (2) the monoclonal antibody concentration in the monoclonal antibody solution ranges from 20 mg/ml to 100 mg/ml;
  (3) the monoclonal antibody solution contains at least a basic amino acid; and
  (4) the zeta potential Ei1 (mV) of the monoclonal antibody in the solution satisfies the following conditions:
   a) $0\,mV \leq Ei1-Em \leq 20\,mV$, with respect to the zeta potential Em (mV) of the virus-removing membrane; and satisfies the following conditions:
   b) $10\,mV \leq Ei0-Ei1 \leq 40\,mV$, with respect to the zeta potential Ei0 (mV) of the monoclonal antibody in the solution (pH=4 and ionic strength of 0.1 mM) containing the monoclonal antibody.

14. The method according to claim 13, wherein the zeta potential Ei1 (mV) of the monoclonal antibody in the monoclonal antibody solution satisfies the following conditions:
   $-4\% \times Em \leq Ei1 \leq -550\% \times Em$, with respect to the zeta potential Em (mV) of the virus-removing membrane.

15. The method according to claim 13, wherein the zeta potential Ei0 (mV) of the monoclonal antibody contained in a solution (pH=4 and ionic strength of 0.1 mM) containing the monoclonal antibody is +25 mV or higher.

16. The method according to claim 13, wherein the antibody throughput is 2 kg/m$^2$/3 hours/bar (based on pressure) or more.

17. The method according to claim 13, wherein filtration using the virus-removing membrane is dead-end filtration.

18. A method for removing viruses by filtering a monoclonal antibody solution containing a monoclonal antibody using a virus-removing membrane, wherein:
  (1) the monomer content of the monoclonal antibody accounts for 90% or more;
  (2) the monoclonal antibody concentration in the monoclonal antibody solution ranges from 20 mg/ml to 100 mg/ml;
  (3) the monoclonal antibody solution contains at least a basic amino acid; and
  (4) the zeta potential Ei1 (mV) of the monoclonal antibody in the solution satisfies the following conditions:
   a) $0\,mV \leq Ei1-Em \leq 20\,mV$, with respect to the zeta potential Em (mV) of the virus-removing membrane; and satisfies the following conditions:
   b) $10\,mV \leq Ei0-Ei1 \leq 40\,mV$, with respect to the zeta potential Ei0 (mV) of the monoclonal antibody in a solution (pH=4 and ionic strength of 0.1 mM) containing the monoclonal antibody.

* * * * *

UNITED STATES PATENT AND TRADEMARK OFFICE
CERTIFICATE OF CORRECTION

PATENT NO. : 9,056,896 B2  
APPLICATION NO. : 13/260419  
DATED : June 16, 2015  
INVENTOR(S) : T. Hongo et al.

It is certified that error appears in the above-identified patent and that said Letters Patent is hereby corrected as shown below:

In the claims,  
Claim 1 (column 17, line 54), please change "$\geq 4$" to --$\geq$ 4--.  
Claim 1 (column 17, line 55), please change "⅔" to --$^2/3$--.  
Claim 12 (column 18, line 63), please change "$\geq 4$" to --$\geq$ 4--.

Signed and Sealed this  
Twenty-second Day of December, 2015

Michelle K. Lee  
*Director of the United States Patent and Trademark Office*